(12) United States Patent
Hoffman et al.

(10) Patent No.: US 9,308,074 B2
(45) Date of Patent: Apr. 12, 2016

(54) FILTER RETRIEVAL DEVICE

(71) Applicant: Cook Medical Technologies LLC, Bloomington, IN (US)

(72) Inventors: Grant T. Hoffman, Bloomington, IN (US); Jeffry S. Melsheimer, Springville, IN (US); Robert Eells, Bloomington, IN (US); Jonathan L. Bennett, Bloomington, IN (US); Brandon Arnett, Gosport, IN (US); Shavonna Warren, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 187 days.

(21) Appl. No.: 13/693,175

(22) Filed: Dec. 4, 2012

(65) Prior Publication Data

US 2014/0155930 A1 Jun. 5, 2014

(51) Int. Cl.
*A61M 29/00* (2006.01)
*A61F 2/01* (2006.01)
*A61B 17/22* (2006.01)
*A61F 2/95* (2013.01)
*A61B 17/00* (2006.01)

(52) U.S. Cl.
CPC .......... *A61F 2/01* (2013.01); *A61B 2017/00358* (2013.01); *A61B 2017/22035* (2013.01); *A61F 2002/011* (2013.01); *A61F 2002/9517* (2013.01); *A61F 2250/0097* (2013.01)

(58) Field of Classification Search
CPC ............... A61F 2/01; A61F 2002/011; A61F 2002/9534; A61F 2002/9528; A61B 2017/00358; A61B 17/32075; A61B 17/320725; A61B 17/221; A61B 2017/22035; A61B 2017/00623; A61B 17/32056

USPC ......... 606/108, 113, 127, 144, 145, 148, 191, 606/194, 198, 200, 207; 623/1.11, 1.12, 623/1.13, 1.23, 2.11
See application file for complete search history.

(56) References Cited

U.S. PATENT DOCUMENTS

| | | | | |
|---|---|---|---|---|
| 1,833,687 | A * | 11/1931 | Neivert ......................... | 606/113 |
| 5,171,233 | A * | 12/1992 | Amplatz et al. ............... | 604/540 |
| 5,342,371 | A * | 8/1994 | Welter et al. .................. | 606/113 |
| 5,911,725 | A * | 6/1999 | Boury ............................ | 606/108 |
| 6,447,530 | B1 | 9/2002 | Ostrovsky et al. | |
| 6,936,054 | B2 * | 8/2005 | Chu .............................. | 606/145 |

(Continued)

FOREIGN PATENT DOCUMENTS

| | | |
|---|---|---|
| EP | 1974692 A1 | 10/2008 |
| WO | WO 99/09921 A1 | 3/1999 |
| WO | WO 2011/094261 A1 | 8/2011 |

OTHER PUBLICATIONS

Extended European Search Report for EP App. No. 13195521.3, mailed May 14, 2014.

*Primary Examiner* — Katherine M Shi
*Assistant Examiner* — Mohamed Gabr
(74) *Attorney, Agent, or Firm* — Brinks Gilson & Lione (57) ABSTRACT

A device for inferior retrieval of a vena cava filter includes an outer sheath with a first radial window closer to the distal end than the proximal end of the outer catheter; an inner sheath generally extending movably inside the lumen of the outer sheath and having a second radial window; and a snare tool having an elongated guide element extending through the inner sheath and a snare loop distally attached to the guide element. The snare loop is extendable outward through the two radial windows.

20 Claims, 4 Drawing Sheets

(56) References Cited

U.S. PATENT DOCUMENTS

| | | |
|---|---|---|
| 7,976,562 B2 | 7/2011 | Bressler et al. |
| 8,043,322 B2 | 10/2011 | Hendriksen et al. |
| 8,231,649 B2 | 7/2012 | Petersen |
| 2006/0149295 A1 | 7/2006 | Fleming, III |
| 2008/0188887 A1 | 8/2008 | Batiste |
| 2009/0099574 A1 | 4/2009 | Fleming, III |
| 2009/0118760 A1 | 5/2009 | Clausen |
| 2009/0182370 A1* | 7/2009 | Volobuyev et al. ........... 606/200 |
| 2011/0022083 A1* | 1/2011 | DiMatteo et al. ............. 606/228 |
| 2012/0109180 A1 | 5/2012 | Shrivastava |

* cited by examiner

FILTER RETRIEVAL DEVICE

TECHNICAL FIELD

The present invention generally relates to a removal device for retrieving an implanted collapsible filter. In particular, the present invention relates to a removal device for inferior removal of an implanted vena cava filter with a superior removal hook and inferior struts.

BACKGROUND

Certain implantable devices, in particular umbrella-like filters or filters with a hub and a plurality of struts extending thereof are designed to be collapsed and removed only from the end with the hub. For a vena cava filter, for example, the typical removal method thus involves approaching the filter from the superior side. A snare may be used to engage the removal hook and to pull the hub into an axial end of a catheter or tube until the inferior struts are collapsed and accommodated in the catheter or tube. Subsequently, the catheter or tube is withdrawn with the filter inside.

There may, however, be situations, in which it is desirable to remove an implanted filter or collapsible device, but the typical method of removal of the device is impossible or not desired.

SUMMARY OF THE INVENTION

The present invention provides a device that is configured for a removal of the implanted device from the end opposite the hub or removal hook.

According to one aspect of the present invention, a device for inferior retrieval of a vena cava filter comprises an outer sheath with a first radial window closer to the distal end than the proximal end of the outer catheter; an inner sheath generally extending movably inside the lumen of the outer sheath; and a snare tool having an elongated guide element extending through the inner sheath and a snare loop distally attached to the guide element, the snare loop extendable outward from an opening in the inner sheath and outward through the first radial window in the outer sheath. The inner sheath provides the benefit that it can be moved to substantially cover the radial opening of the outer sheath to form a substantially flush outer cylindrical surface.

According to another aspect of the invention, the opening in the inner sheath may be a second radial window closer to the distal end than the proximal end of the inner sheath. By providing two radial windows, one in the outer sheath and one in the inner sheath, these windows can be easily aligned with each other to create an overlap by a relative movement between the outer sheath and the inner sheath.

According to a further aspect of the invention, the second radial window may have a shape facilitating an insertion of the vena cava filter. For example, the second radial window may have a generally half-oval shape. It may further have an edge with a flared edge portion that extends at least across a distal portion of the edge. The flared edge portion may, for example, protrude outward from the first radial window when the flared edge portion resides in a longitudinal and angular position within the first radial window.

According to yet another aspect of the invention, the first radial window is an oval cutout. This shape is easy to manufacture and complements the shape of the first radial window. Further, to optimize the cross-section of the oval cutout, it may extend circumferentially across about half of the circumference of the first sheath.

According to another aspect of the invention, the snare loop may have a relaxed shape, in which the snare loop forms a radially deflected loop. Such a preshaped loop makes it easier to maneuver the snare loop outward through the first radial window. Further, the snare tool may comprise a snare hub having a proximal end distally attached to the elongated guide and securing the snare loop to the elongated guide. The snare loop may extend distally or proximally from the snare hub. If the snare loop extends from the proximal end of the snare hub, a distal movement of the hub and the snare loop is less likely to cause any entanglement of the snare loop inside the inner sheath.

According to a further aspect of the invention, the inner sheath may be configured to be moved longitudinally or rotationally relative to the outer sheath, or longitudinally and rotationally.

According to yet another aspect of the invention, a first handle is proximally attached to the outer sheath, a second handle with an axial channel is proximally attached to the inner sheath, and a third handle is proximally attached to the snare tool. The second and third handles are preferably configured to be longitudinally and rotationally manipulated relative to the first handle and to each other. These independently operable handles allow for a highly precise placement and operation of the removal tool.

According to a further aspect of the invention, angular markings on at least one of the first handle, the second handle, and the third handle facilitate angular alignment of at least one of the first radial window, the second radial window, and the snare tool. Additionally or alternatively, at least one marker on at least one of the outer sheath, the inner sheath, and the snare tool provides information aiding proper positioning of the device. The marker may be radiopaque or echogenic or distinguishable by any available imaging method.

According to yet another aspect of the invention, a method of removing an implantable device having proximally extending radially collapsible struts, a distal hub and a removal hook distally attached to the hub, the method comprising the steps of providing an outer sheath with a first lumen longitudinally extending from a first proximal end to a first distal end, the outer sheath having a first radial window between the first proximal end and the first distal end, the first radial window being closer to the first distal end than the first proximal end; providing an inner sheath generally extending inside the lumen of the outer sheath, the inner sheath having a lumen extending from a second proximal end to a second distal end, the inner sheath having a second radial window between the second proximal end and the second distal end; providing a snare tool having an elongated guide element extending through the inner sheath and a snare loop distally attached to the guide element; advancing the outer sheath, the inner sheath and the snare tool distally past the removal hook of the implantable device until the first radial opening is positioned distally from the implantable device; aligning the first and second radial openings to obtain an overlap with each other; extending the snare loop outward through the first and second radial openings; engaging the removal hook with the snare loop; distally moving the snare tool relative to the outer and inner sheaths so as to distally pull the implantable device into the inner sheath until the proximal struts are substantially accommodated within the inner sheath; moving the inner sheath relative to the outer sheath until the overlap between the first radial opening and the second radial opening is substantially reduced; and proximally withdrawing the outer sheath along with the inner sheath, the snare tool and the implantable device.

Further details and benefits of the present invention become apparent from the following description of the attached drawings.

DETAILED DESCRIPTION OF THE DRAWINGS

The included drawings are provided for purely illustrative purposes and are not intended to limit the scope of the invention. While the following description is provided by a specific example of a vascular filter for implantation in a blood vessel, the present invention is not limited to vascular applications or specific filters and is applicable to collapsible implantable devices designed for collapsing from one side but not the other.

Figure 1:
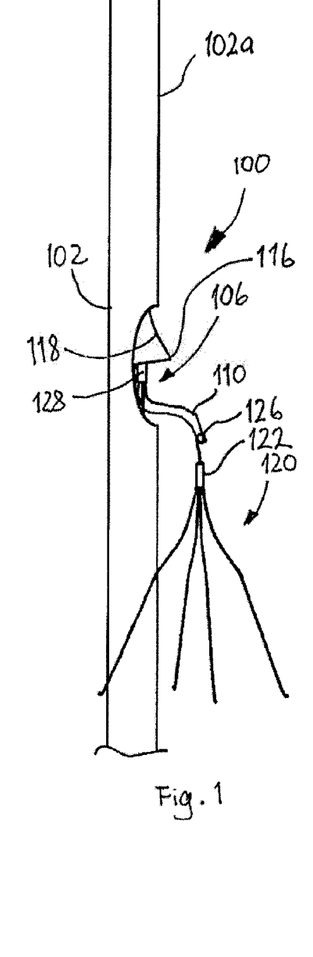
FIG. 1 shows a device for inferior filter retrieval with a snare loop engaging a removal hook of a vena cava filter according to one embodiment of the invention.
Figure 6:
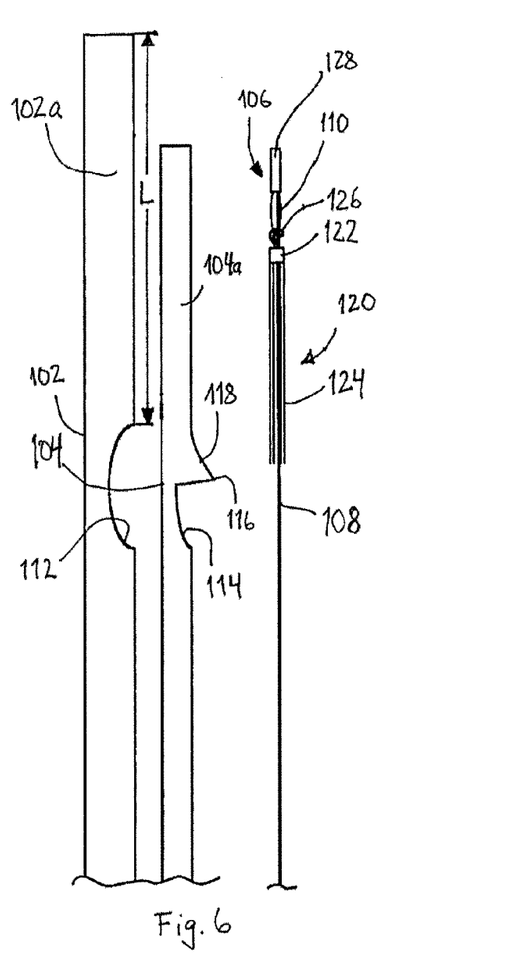
FIG. 6 shows individual elements of the inferior filter retrieval device of FIG. 1 and a collapsed filter.

Now referring to FIGS. 1 and 6, a inferior filter retrieval device 100 comprises an outer sheath 102, and inner sheath 104, and a snare tool 106, of which an elongated guide member 108 extends through the inner sheath 104 and a snare loop 110 is visible in FIG. 1.

In the embodiment shown in the drawing, the outer sheath 102 has an outer diameter of about 5 mm, and the inner sheath has an outer diameter of about 4 mm. The inner sheath 104 has an interior diameter of about 3 mm. These dimensions are variable, depending on the specific application as will be explained below in greater detail.

The outer sheath has a first radial opening 112. In the embodiment shown, the first radial opening 112 is formed by an oval cut-out portion of the outer sheath 102. In the circumferential direction, the width of the first radial opening 112 covers about half of the circumference of the outer sheath 102. The first radial opening 112 as shown has a length that is about three times as great as its width. These dimensions are variable. Generally, the first radial opening 112 is preferably at least twice as long as it is wide for ease of inserting a filter 120 as will be explained below.

The inner sheath 104 has a second radial opening 114. In the embodiment shown, the second radial opening 114 is formed by a generally straight radial cut at the distal side of the second radial opening and by an arc at the proximal side. The resulting shape of the second radial opening 114 resembles a half-moon or a half oval. Alternatively, the generally straight radial cut may also be curved to form a concave or convex edge with a curve radius that is generally smaller than the curve radius of the arc-shaped side. The arc and the optional curved edge of the second radial opening 114 may be formed by cutting the inner sheath 104 at an acute or obtuse angle relative to the central longitudinal axis of the inner sheath 104. The width of the second radial opening 114 may extend over a similar angular range as the first radial opening, in this embodiment over about 180°, thus about half of the circumference of the inner sheath 104. The length of the second radial opening 114 may be shorter than that of the first radial opening, but is preferably at least about half of the length of the first radial opening 112.

On its distal side, the second radial opening 114 has an outward flare 116 along its distal edge. The flare 116 is formed by a distal gradual expansion 118 of the inner sheath 104 toward the distal side of the second radial opening 114. The flare 116 forms the largest diameter of the expansion 118 and protrudes radially outward through the first radial opening 112. Although the flare 116 protrudes radially beyond the lumen of the outer sheath 102, the inner sheath 104 is flexible and bendable enough to accommodate the flare inside the lumen of the outer sheath 102 upon distal or rotational movement of the inner sheath inside the outer sheath.

In FIG. 1, the snare tool 106 is shown inserted into the inner sheath 104. The snare loop 110 is held by a distal snare hub 128 (visible in FIG. 6). As will be described below, the snare loop 110 may also be attached to the distal side of the snare hub 128.

At least the outer sheath 102 has a distal portion 102a extending distally from the first radial opening 112 by a length that corresponds to at least the length of a collapsed device to be removed by the inferior filter retrieval device in addition to the collapsed length of the snare loop 110 and any additional distal length of the snare tool 106. The inner sheath 104 may extend distally by a different or the same length. The distal portion of the inner sheath on the distal side of the second radial opening 114 may slightly shorter than that of the distal portion 102a to allow for some distal movement of the inner sheath 104 inside the outer sheath 102 without distally emerging from the outer sheath 102. These dimensions allow for distally moving the second radial opening 114 past the first radial opening 112 for obtaining a generally closed, nearly flush outer surface of the inner and outer sheaths 102 and 104.

The inferior filter retrieval device 100 may be adapted for removing a customary vena cava filter 120 or a different collapsible device. The filter 120 as shown has a superior hub 122 with a plurality of inferior struts 124. A removal hook 126 is fastened to the superior end with the hub 122.

As illustrated in FIG. 6, the filter 120 of the shown embodiment has a collapsed length, extending from the superior removal hook 126 to the inferior end of the struts 124, that is preferably accommodated inside the removal tool 100 upon retrieval. Accordingly, the length L of the distal portion 102a of the outer sheath 102, extending from the first radial opening 112 to the distal end of the outer sheath 102, is at least as long as the combined lengths from the distal end of the snare hub 128 to the proximal end of the snare loop 110 and from the superior removal hook 126 to the inferior ends of the struts 124 of the filter 120. A corresponding distal portion 104a extending from the second radial opening 114 to the distal end of the inner sheath 104 may have a length that is shorter than the distal portion 102a by at least the length of the second radial opening 114 so that the distance from the distal end of the inner sheath to the proximal edge of the second radial opening is about equal to or slightly shorter than the length L. This allows form accommodating the entire length of the second radial opening 114 inside the distal length 102a of the outer sheath. But it is within the scope of the present invention if the distal lengths 104a and 102a deviate from these considerations.

FIGS. 1 through 5 illustrate retrieval steps of a inferior retrieval of the vena cava filter 120. These steps can be applied in analogy to the retrieval of any other filter or collapsible device that provides for a removal only in one direction and resists collapsing in the other direction.

Now referring to FIG. 1, the outer sheath 102 accommodating the inner sheath 104 surrounding the snare tool 106 is inserted from the inferior side (corresponding to the bottom of the drawing) in the superior direction (upward) into the vicinity of the vena cava filter 120. The outer sheath is distally moved past the filter 120 to an extent that the snare loop 110 can be manipulated to engage the superior hook 126.

Figure 8:
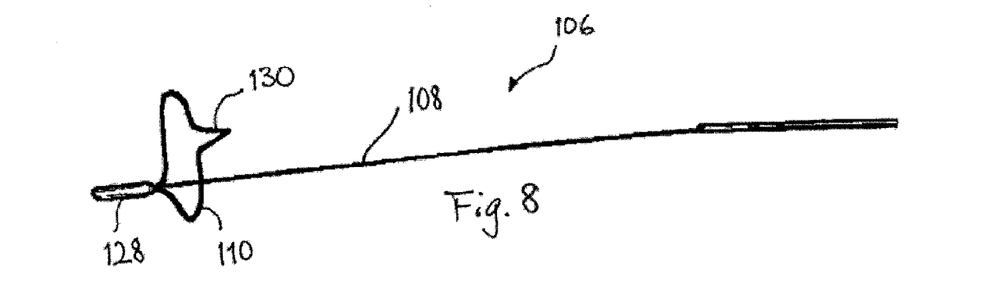
FIG. 8 shows one embodiment of a snare tool for use in a inferior filter retrieval device.

As shown in FIG. 8, the snare loop 110 preferably has a relaxed shape that forms a generally radially extending loop. At a radial side remote from the snare hub 128, the loop 110 has an indentation 130 forming an angled, v-shaped bend in the proximal direction. The indentation 130 facilitates an engagement of the snare loop 110 with the removal hook 126. Once any portion of the snare loop 110 has been maneuvered inside the hook 126, a distal movement of the snare tool 106 will slide the hook 126 toward the proximal angle of indentation 130.

Figure 2:
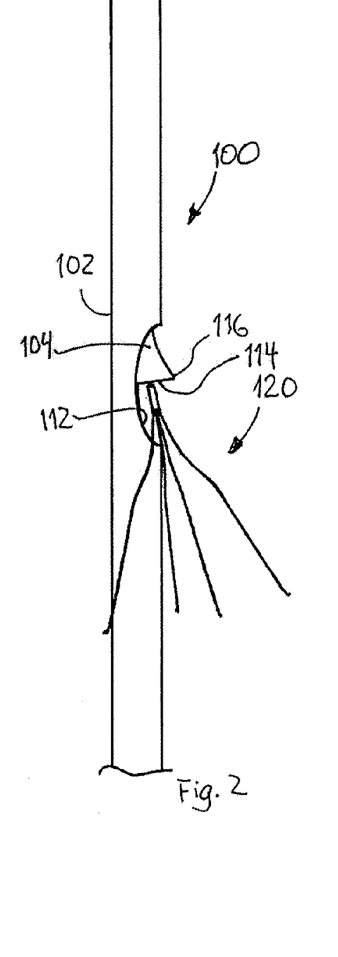
FIG. 2 shows the inferior filter retrieval device of FIG. 1 in the process of pulling the vena cava filter into an inner sheath of the removal device.

Now referring to FIG. 2, a further distal movement of the snare tool 106 pulls the hook 126 distally into the inner sheath 104. The flare 116 operates like a funnel and eases the introduction of the filter 120 into the inner sheath 104 by providing an enlarged radial cross-section of the second radial opening 114. The first radial opening 112 and the second radial opening 114 extend proximally from the flare 116 far enough to provide a sufficient longitudinal dimension of the first and second radial openings 112 and 114 for introducing the filter 120 into the inner sheath 104.

Figure 3:
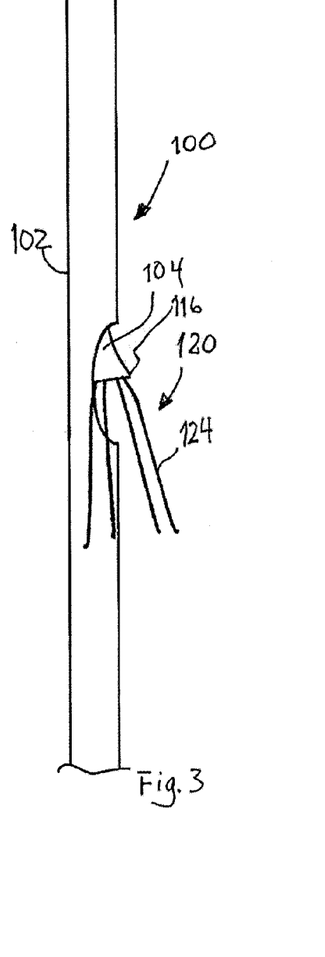
FIG. 3 shows the inferior filter retrieval device of FIG. 1 at an advanced stage of the process of pulling the vena cava filter into the inner sheath of the removal device.

Now referring to FIG. 3, a further distal movement of the snare tool 106 moves the filter 120 so far into the inner sheath 104 that the flare 116 contacts the struts 124 and forces the struts to move toward a collapsed position, in which the struts 124 extend generally parallel to each other.

Figure 4:
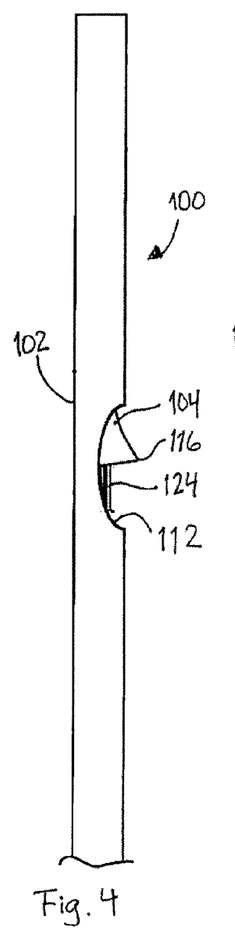
FIG. 4 shows the inferior filter retrieval device of FIG. 1 after the vena cava filter has been accommodated inside the inner sheath of the removal device.

As shown in FIG. 4, once the inferior ends of the struts 124 have entered the inner sheath 104, only the flare 116 formed on the inner sheath 104 protrudes radially from the first opening 112.

Figure 5:
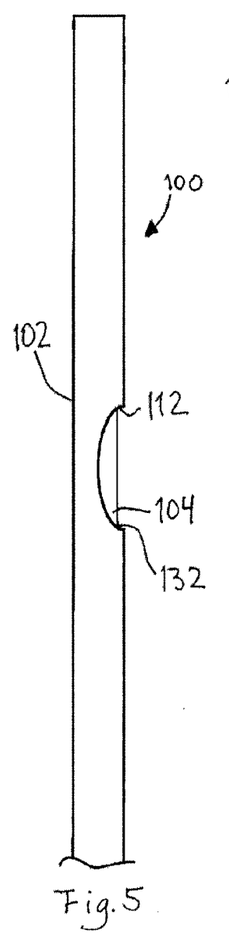
FIG. 5 shows the inferior filter retrieval device of FIG. 1 after the inner sheath of the removal device has been moved relative to an outer sheath to close a radial opening in the outer sheath.

Subsequently, as illustrated in FIG. 5, the inner sheath 104 may be distally moved relative to the outer sheath 102 until the proximal edge of the second radial opening 114 reaches or passes the distal edge of the first radial opening 112. Alternatively or additionally, the inner sheath 104 may be rotated relative to the outer sheath 102 so that the second radial opening 114 is oriented opposite to the first radial opening. As noted above, the flare 116 is flexible so that it deforms to fit inside the lumen of the outer sheath 102. After one or both of the relative movements between the outer and the inner sheaths 102 and 104, the first radial opening is closed. The inner sheath 104 covers the first radial opening 112 so that a nearly flush outer surface results. The surface of the inner sheath is slightly recessed relative to the surface of the outer sheath 102. This recess 132 corresponds to the wall thickness of the outer sheath and may be further ameliorated by providing the first radial opening 112 with a tapered edge. Generally, however, the recess 132 does not inhibit a smooth proximal removal of the inferior removal tool 100 from the location.

Figure 7:
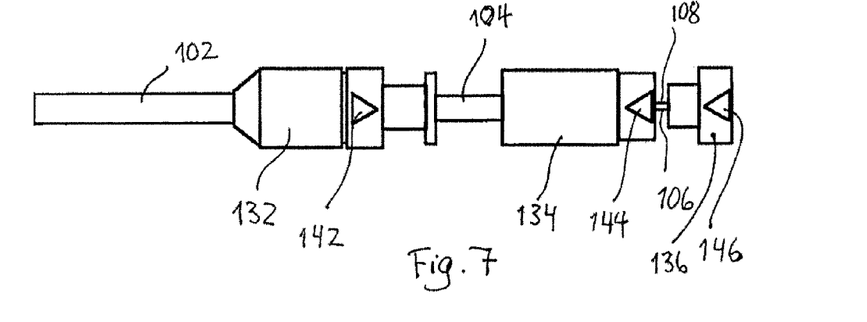
FIG. 7 shows a proximal handle arrangement of a inferior filter retrieval device according to one embodiment of the invention.

FIG. 7 illustrates one schematic example of a proximal handle 140 for manipulating the outer sheath 102, the inner sheath 104, and the snare tool 106 relative to one another.

On the left side of FIG. 7, the outer sheath 102 is shown. At its proximal end, the outer sheath is durably, but preferably removably, connected to a first handle 132 bearing a first angular marker 142. The angular marker may mark the angular location of the first radial opening 102. The inner sheath 104 is inserted into the outer sheath 102 and extends coaxially therewith. The inner sheath 104 emerges proximally from the handle 132 and is proximally connected to a second handle 134. The inner sheath is movable in a longitudinal direction and rotationally relative to the outer sheath 102 and to the first handle 132. The second handle 134 bears a second angular marker 144 that has an angular position coinciding with that of the second radial opening 114. On the proximal side of the second handle 134, the snare tool 106 emerges from the second handle 134. Only a portion of the elongated guide member 108 of the snare tool 106 is visible in FIG. 7. The remainder of the elongated guide member 108 extends distally through the inner sheath 104 to the first and second radial openings 112 and 114 (not shown in FIG. 7). The guide member 108 is proximally connected to a third handle 136. The snare tool 106 is movable in a longitudinal direction and rotationally relative to the inner and the outer sheaths 102 and 104. The third handle 136 bears a third angular marker 146 that has an angular position coinciding with that of the indentation 130.

A manipulation of the first handle 132 moves the outer sheath 102. Thus, the first handle is usually maneuvered at the beginning of a removal procedure for proper placement of the first radial opening 112 and then again at the end of the removal procedure for withdrawing the removal device 100. The second handle 134 operates the inner sheath 106 and is thus used to position the second radial opening 114 before or after placing the outer sheath. The second handle is also used after accommodating the filter 120 in the inner sheath to close the first radial opening 112 by moving the second radial opening 114 away from the first radial opening 112. The third handle 136 operates the snare tool for engaging the removal hook and for pulling the filter 120 distally into the inner sheath 104.

Additionally or alternatively, further markings may be applied around the first and second radial openings 112 and 114 as well as on the snare loop 110. These further markings may be radiopaque or echogenic or may contain a material or texture that is distinguishable from a background by customary imaging methods.

Now referring to FIG. 8, the snare loop 110 of the snare tool 106 may be secured to the snare hub 128 at the proximal end thereof. The v-shaped indentation 130 is thus bent in the proximal direction, and the elongated guide member 108 extends from the proximal side of the snare hub 128.

The snare tool 106 shown in FIG. 8 has a preshaped snare loop 110. Preferably, the snare loop 110 is shaped before the snare hub 128 is permanently attached to the snare loop 110, for example by soldering or another biocompatible method. For example, the radially remote end of the snare loop 110 that forms the indentation 130 may be folded first. Then the snare loop 110, starting from the indentation 130, is rolled up on a cylindrical object until the snare loop 110 retains a shape similar to one the shapes shown in FIG. 8.

Figure 9:
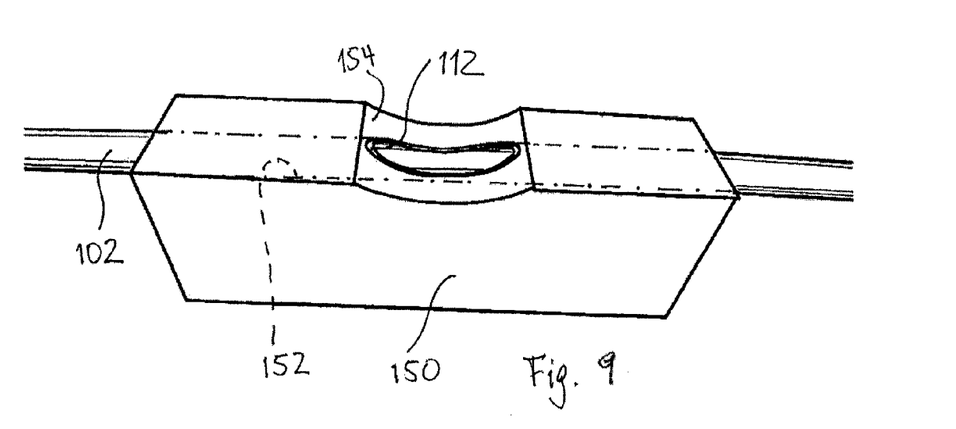
FIG. 9 illustrates one embodiment of a manufacturing process for producing the outer sheath of a inferior filter retrieval device.
Figure 10:
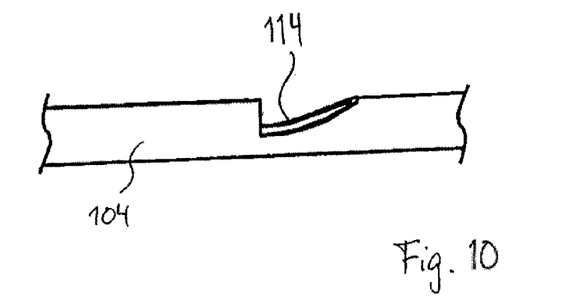
FIG. 10 illustrates one embodiment of a manufacturing process for producing the inner sheath of a inferior filter retrieval device.

FIGS. 9 and 10 illustrate a method of manufacturing the first and second radial openings 112 and 114 in the outer and inner sheaths 102 and 104. A skiving block 150 has a transverse bore 152 (indicated with a broken line) that has a diameter dimensioned to accommodate the outer sheath 102. The skiving block 150 further has a cutting recess 154 shaped similar to a partial hollow cylinder with a cylindrical axis perpendicular to the transverse bore 152. The cutting recess 154 intersects the transverse axis 152 in a way that a portion of the wall of the transverse bore 152 is removed over an area that is shaped like the first radial opening 112.

The first radial opening is produced by introducing the outer sheath 102 into the skiving block to a position, in which the intended location of the first radial opening 112 coincides with the area, in which the wall of the transverse bore is removed. A cutting tool is then driven along the curved surface of cutting recess 154 so as to cut away the portion of the outer sheath 102 that protrudes into the cutting recess 154.

The second radial opening 114 in the inner sheath 104 as shown in FIG. 10 may be cut simultaneously with or subsequent to the first radial opening 112. For proper fit, the inner sheath 104 is inserted into the outer sheath 102, which in turn is positioned in the skiving block 150. The position intended for the second radial opening 114 is aligned with the position of the first radial opening 112. The cutting tool is initially only driven across half of the cutting recess 154 so as to cut half of the first radial opening 112 and the oval portion of the second radial opening. Then the inner sheath 104 is removed from the outer sheath. An approximately radial cut connecting the ends of the previously set curved cut completes the second radial opening, resulting in a shape as shown in FIG. 10. The flare 116 is then formed in the location of the approximately radial cut by inserting a cylindrical or otherwise suitably shaped tool into the second radial opening 114, applying heat, and bending the wall to the inner sheath 104 outward proximate the generally radial cut to form the flare 116 and the gradual expansion 118 of the diameter of the inner sheath 104. The inner sheath 104 is made of a thermoplastic material so that the deformation under heat is a plastic deformation. Cooling the deformed inner sheath 104 makes the flare permanent. The heat may be applied with a flare gun, for example at a temperature of about 500° F. to about 600° F. The temperature chosen depends on the material, from which the inner sheath 104 is manufactured.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A device for inferior retrieval of a vena cava filter, the device comprising:

an outer sheath with a first lumen longitudinally extending from a first proximal end to a first distal end, the outer sheath having a first radial window between the first proximal end and the first distal end, the first radial window being closer to the first distal end than the first proximal end;

an inner sheath generally extending movably inside the lumen of the outer sheath, the inner sheath having a lumen extending from a second proximal end to a second distal end, the inner sheath forming an opening being a second radial window between the second proximal end and the second distal end, the second radial window being closer to the second distal end than the second proximal end, the second radial window formed by an edge with a flared edge portion that extends at least across a distal portion of the edge, the flared edge portion being flexible such that it can deform to fit within the first lumen of the outer sheath, the flared edge portion protrudes outward from the first radial window when the flared edge portion resides in a longitudinal and angular position within the first radial window; and a snare tool having an elongated guide element extending through the inner sheath and a snare distally attached to the guide element, the snare extendable outward from the second radial window in the inner sheath and outward through the first radial window in the outer sheath.

2. The device according to claim 1, wherein the second radial window is generally shaped like a half-oval.

3. The device according to claim 1, wherein the first radial window is an oval cutout.

4. The device according to claim 3, wherein the oval cutout extends circumferentially across about half of the circumference of the outer sheath.

5. The device according to claim 1, wherein the snare has a relaxed shape, in which the snare loop forms a radially deflected loop.

6. The device according to claim 5, wherein the snare tool further comprises a snare hub having a proximal snare end distally attached to the elongated guide and securing the snare loop to the elongated guide.

7. The device according to claim 1, wherein the snare loop extends from a proximal end of the elongated guide element.

8. The device according to claim 1, wherein the inner sheath is configured to be longitudinally moved relative to the outer sheath.

9. The device according to claim 1, wherein the inner sheath is configured to be rotationally moved relative to the outer sheath.

10. The device according to claim 1, further comprising a first handle proximally attached to the outer sheath, a second handle with an axial channel proximally attached to the inner sheath, and a third handle proximally attached to the snare tool, the second and third handles configured to be longitudinally and rotationally manipulated relative to the first handle and to each other.

11. The device according to claim 10, further comprising angular markings on at least one of the first handle, the second handle, and the third handle for angular alignment of at least one of the first radial window, the second radial window, and the snare tool.

12. The device according to claim 1, further comprising at least one marker distinguishable by imaging on at least one of the outer sheath, the inner sheath, and the snare tool.

13. The device of claim 1, wherein the inner sheath has an expansion extending to the flared edge portion, the expansion having a first diameter distally decreasing from the flared edge portion.

14. The device of claim 1, wherein the opening is formed by a proximal side and a distal side, the distal side being the flared edge portion facing the proximal side being an arc.

15. A method of removing an implantable device having proximally extending radially collapsible struts, a distal hub and a removal hook distally attached to the hub, the method comprising the steps of:
  providing an outer sheath with a first lumen longitudinally extending from a first proximal end to a first distal end, the outer sheath having a first radial window between the first proximal end and the first distal end, the first radial window being closer to the first distal end than the first proximal end;
  providing an inner sheath generally extending inside the lumen of the outer sheath, the inner sheath having a lumen extending from a second proximal end to a second distal end, the inner sheath forming a second radial window between the second proximal end and the second distal end, the second radial window being closer to the second distal end than the second proximal end, the second radial window formed by an edge with a flared edge portion that extends at least across a distal portion of the edge, the flared edge portion being flexible such that it can deform to fit within the first lumen of the outer sheath, the flared edge portion protrudes outward from the first radial window when the flared edge portion resides in a longitudinal and angular position within the first radial window; and
  providing a snare tool having an elongated guide element extending through the inner sheath and a snare loop distally attached to the guide element;
  advancing the outer sheath, the inner sheath and the snare tool distally past the removal hook of the implantable device until the first radial window is positioned distally from the implantable device;
  aligning the first and second radial windows to obtain an overlap with each other;
  extending the snare loop outward through the first and second radial windows;
  engaging the removal hook with the snare loop;
  distally moving the snare tool relative to the outer and inner sheaths so as to distally pull the implantable device into the inner sheath until the proximally extending radially collapsible struts are substantially accommodated within the inner sheath;
  moving the inner sheath relative to the outer sheath until the overlap between the first radial window and the second radial window is substantially reduced; and
  proximally withdrawing the outer sheath along with the inner sheath, the snare tool and the implantable device.

16. The method of claim 15, wherein the inner sheath is moved relative to the outer sheath by a rotational relative movement.

17. The method of claim 15, wherein the inner sheath is moved relative to the outer sheath by a longitudinal relative movement.

18. A device for inferior retrieval of a vena cava filter, the device comprising:
  an outer sheath with a first lumen longitudinally extending from a first proximal end to a first distal end, the outer sheath having a first radial window between the first proximal end and the first distal end, the first radial window being closer to the first distal end than the first proximal end;
  an inner sheath generally extending movably inside the lumen of the outer sheath, the inner sheath having a lumen extending from a second proximal end to a second distal end, the second proximal and distal ends being maintained inside the outer sheath, the inner sheath forming an opening between the second proximal and distal ends, the opening formed by an edge with flared edge portion that extends at least across a distal portion of the edge, the a flared edge portion being flexible such that it can deform to fit within the first lumen of the outer sheath in a first configuration, the flared edge portion exits the first radial window in a second configuration while the distal end of the inner sheath remains within the first lumen of the outer sheath; and
  a snare tool having an elongated guide element extending through the inner sheath and a snare distally attached to the guide element, the snare extendable outward from the opening in the inner sheath and outward through the first radial window in the outer sheath.

19. The device according to claim 18, wherein the opening in the inner sheath is a second radial window between the second proximal end and the second distal end, the second radial window being closer to the second distal end than the second proximal end.

20. The device according to claim 18, wherein the flared edge portion protrudes outward from the first radial window when the flared edge portion resides in a longitudinal and angular position within the first radial window.

* * * * *